(12) United States Patent
Mergens et al.

(10) Patent No.: US 6,358,526 B1
(45) Date of Patent: Mar. 19, 2002

(54) METHOD OF MAKING TABLETS AND TABLET COMPOSITIONS PRODUCED THEREFROM

(75) Inventors: William J. Mergens, West Palm Beach, FL (US); Kuei Tu Chang, Mountain Lakes, NJ (US); Gerald T. Holly, Delray Beach, FL (US)

(73) Assignee: Rexall Sundown, Boca Raton, FL (US)

( * ) Notice: Subject to any disclaimer, the term of this patent is extended or adjusted under 35 U.S.C. 154(b) by 0 days.

(21) Appl. No.: 09/639,780

(22) Filed: Aug. 16, 2000

(51) Int. Cl.$^7$ .............................. A61K 9/20; A61K 9/16; A61K 9/36
(52) U.S. Cl. ...................... 424/464; 424/489; 424/479; 514/54
(58) Field of Search ................................ 424/489, 464, 424/479; 514/54

(56) References Cited

U.S. PATENT DOCUMENTS

| | | | |
|---|---|---|---|
| 4,820,522 A | 4/1989 | Radebaugh et al. | 424/468 |
| 5,073,380 A | 12/1991 | Babu et al. | 424/472 |
| 5,079,007 A | 1/1992 | Putnam | 424/422 |
| 5,302,396 A | 4/1994 | Phadke et al. | 424/465 |
| 5,422,122 A | 6/1995 | Powell | 424/465 |
| 5,437,873 A | 8/1995 | Phadke et al. | 424/465 |
| 5,455,047 A | 10/1995 | Bequette et al. | 424/476 |
| 5,587,363 A | 12/1996 | Henderson | 514/54 |
| 5,605,891 A | 2/1997 | Prino et al. | 514/54 |
| 5,635,208 A | 6/1997 | Parekh et al. | 424/451 |
| 5,660,860 A | 8/1997 | Fielden | 424/464 |
| 5,670,168 A | * 9/1997 | Baichwal et al. | 424/464 |
| 5,804,594 A | 9/1998 | Murad | 514/474 |
| 5,840,715 A | 11/1998 | Florio | 514/63 |
| 5,843,919 A | 12/1998 | Burger | 514/62 |
| 5,849,336 A | 12/1998 | Aoygi et al. | 424/570 |
| 5,948,437 A | 9/1999 | Parikh et al. | 424/464 |
| 6,063,403 A | 5/2000 | de Haan et al. | 424/464 |
| 6,106,865 A | * 8/2000 | Stanifort et al. | 424/489 |
| 6,149,938 A | * 11/2000 | bonadeo et al. | 424/464 |

* cited by examiner

Primary Examiner—Diana Dudash
Assistant Examiner—Mina Haghighation
(74) Attorney, Agent, or Firm—Woodcock Washburn LLP

(57) ABSTRACT

The present invention provides a method of making tablet compositions that are substantially free of excipients. The method includes forming a compactable granular mixture containing at least one compaction enhancing therapeutic compound, at least one other therapeutic compound that is different form the compaction enhancing therapeutic compound, and less than about 15 weight percent of a non-aesthetic excipient. The compactable granular mixture thus obtained is compressed to form a tablet composition. The present invention also provides tablet compositions produced by the methods of the present invention that are substantially free of excipients.

38 Claims, No Drawings

METHOD OF MAKING TABLETS AND TABLET COMPOSITIONS PRODUCED THEREFROM

FIELD OF THE INVENTION

The present invention relates to a method for making tablets, and more particularly, relates to a method for making tablets that are substantially free of excipients, where at least one therapeutic compound in the tablet serves as a compaction enhancing agent for the tablet. The present invention also relates to tablet compositions produced by the methods of the present invention.

BACKGROUND OF THE INVENTION

Tablet compositions are commonly used to deliver therapeutic compounds to a patient such as a human or animal. By "tablet" as used herein, it is meant solid particles, containing or including therapeutic compounds, that are compressed under pressure into any desirable shape, such as a pill or caplet.

Typically, tablets contain other ingredients, hereinafter referred to as "excipients," that provide necessary physical or aesthetic properties to a tablet for delivery of the therapeutic compound. For example, with respect to physical properties, tablets generally need to have acceptable hardness, disintegration, dissolution rate for release of the therapeutic, friability, stability, and size to effectively deliver a therapeutic compound. With respect to aesthetics, it may be desirable for the tablet to contain additives that appeal to the human senses such as colorants, fragrances, texture modifiers, and/or flavorants. Specific types of excipients commonly used in tablet compositions include for example diluents, binders, lubricants, glidants, disintegrants, gelling agents, flavoring agents, and coloring agents. Many of these excipients are commonly added because the therapeutic compound alone may have poor compactability, and thus excipients are needed to achieve the desired tabletting performance.

A problem, however, in using excipients, is that the tablet may become too large to ingest due to the amount of excipients needed to effectively formulate the tablet. A solution to this problem would be to reduce the amount of therapeutic compound and excipients to reduce the overall weight of the tablet, however, multiple tablets would then be needed to deliver the appropriate amount of therapeutic compound. Another problem in using excipients is that, particularly in nutraceuticals, they do not adequately compensate for low density of many herbal products and as such, are in many cases unsatisfactory solutions to tabletting problems. Additionally, excipients often add cost to the tablet, and also may be objectionable to some consumers.

Tablet formulations in which it is especially desirable to reduce the amount of excipients are those used for the treatment of connective tissue to prevent, repair, or lessen ailments of the joints and cartilage tissue, such as observed with arthritis. For example, U.S. Pat. Nos. 5,364,845 and 5,587,363 both to Henderson ("Henderson") disclose therapeutic compositions for the treatment and repair of connective tissue containing amino sugars such as glucosamine, and glycosaminoglycans such as chondroitin. The compositions disclosed in Henderson are used in the form of a powder (for large animals) or capsule (for small animals). Additionally, it is known that these same compositions can be supplied in tablet form, if excipients are used. For example, the commercially available product called "Osteo-Bi-flex" supplied by Rexall Sundown, provides in tablet form a composition containing glucosamine, chondroitin sulfate, and excipients, where the excipients make up at least 23 wt % of the tablet formulation.

U.S. Pat. No. 5,843,919 to Burger discloses a composition and method for the treatment of arthritis where the composition contains one or more glucosamines and one or more omega-3-fatty acids. Although Burger discloses that a tablet can be prepared, it is apparent that excipients would be needed as Burger discloses that the glucosamine is preferably dissolved in an oil containing the omega-3-fatty acid.

Other compositions, which may optionally be in the form of tablets, for treating ailments of the joints and connective tissues are disclosed in for example U.S. Pat. No. 5,605,891 to Prino et al., U.S. Pat. No. 5,840,715 to Florio, and U.S. Pat. No. 5,849,336 to Aoyagi et al. These patents however, provide no specific example of useful tablet formulations.

Amino sugars and glycosaminoglycans have also been used in compositions for treating skin. For example, U.S. Pat. No. 5,804,594 to Murad discloses a composition for the prevention and treatment of skin conditions that contain a sugar compound, an antioxidant, an amino acid, a transition metal component, a catechin based preparation, a glucosamine and chondroitin. Although tablet formulations are disclosed, it is taught that such compositions need to be prepared in the presence of carriers.

With respect to other therapeutics, it is known that a therapeutic alone may be compressible, without excipients. For example, U.S. Pat. No. 5,079,007 to Putnam discloses an implant containing a crystalline salt of cephalosporin, an amorphous salt of cephalosporin and from 0 to 10 weight percent excipients. Putnam teaches that the crystalline and amorphous cephalosporin forms are compressible alone to form a tablet, and that the ratio of the two components are adjusted to obtain the desired release characteristics of the implant. Putnam thus does not describe a method for making a tablet where one therapeutic compound serves as a compaction enhancing agent for a different therapeutic compound.

Thus, it would be desirable to develop a method of making tablets and tablet compositions produced therefrom that are substantially free of excipients, where at least one of the therapeutic compounds is a compaction enhancing agent for the other therapeutic compound.

SUMMARY OF THE INVENTION

The present invention provides a method of making tablets that are substantially free of excipients. The method of the present invention includes forming a compactable granular mixture comprising (i) at least about 3 weight percent of a compaction enhancing therapeutic compound, (ii) at least one other therapeutic compound that is different from the compaction enhancing therapeutic compound and (iii) less than about 15 weight percent of non-aesthetic excipients. The compactable granular mixture is compressed to form one or more tablets.

In a preferred embodiment of the present invention, the compaction enhancing therapeutic compound includes a glycosaminoglycan and the other therapeutic compound includes an amino sugar.

The present invention also provides a tablet composition containing from about 3 weight percent to about 99.5 weight percent of a compaction enhancing therapeutic compound; from about 0.5 weight percent to about 97 weight percent of at least one second therapeutic compound that is different from the compaction enhancing therapeutic compound; and less than about 15 weight percent excipients. The compaction enhancing therapeutic compound enhances the compaction of the second therapeutic compound and is preferably in intimate admixture with the second therapeutic compound.

DETAILED DESCRIPTION OF THE INVENTION

The present invention provides a method of making tablets that are substantially free of excipients. The tablets produced by the method of the present invention contain at least two therapeutic compounds, where at least one of the therapeutic compounds serves as a compaction enhancing agent for the other therapeutic compound. By being able to provide tablets that are substantially free of excipients, smaller tablets and/or tablets containing greater amounts of therapeutic compounds can be produced. Thus, tablets can be provided that are more easily ingested due to the smaller size, and/or eliminating the need for taking multiple tablets to obtain a desired dosage of a therapeutic compound.

By "substantially free" of excipients it is meant that the tablet contains less than about 15 weight percent, more preferably less than about 8 weight percent, and most preferably less than about 2 weight percent excipients, based on the total weight of the tablet on a dry basis (i.e., excluding moisture as hereinafter defined). The term "excipient," as used herein refers to any additive, liquid or solid, present in the tablet that provides some non-therapeutic property to the tablet. For example, excipients are usually added to enhance mechanical or aesthetic properties in a tablet, or to dilute the therapeutic compound. As such, the term excipient, as used herein, does not include therapeutic compounds, or moisture, such as water or other solvent, that is used during the manufacture of the tablet, or is inherently present in one of the ingredients used to form the tablet. Common mechanical excipients include for example binding agents, lubricants, disintegrants, coating agents, gelling agents, glidants, absorbents, surfactants, antiadherents, or combinations thereof. Common aesthetic excipients include for example colorants, flavorants, or combinations thereof. Common excipients used to dilute the therapeutic compound include for example diluents, fillers, or combinations thereof. Preferably, the tablet contains less than about 15 wt %, more preferably less than 8 wt %, and most preferably less than about 2 wt % mechanical or diluting excipients (i.e., non-aesthetic excipients) based on the total weight of the tablet on a dry basis.

By "therapeutic compound" it is meant any substance used to treat (including prevent, diagnose, alleviate, or cure) a malady, affliction, nutritional deficiency, disease or injury in a patient. The term "therapeutic compound" is also meant to include substances that are a supplement for improving the nutritional, physical, or emotional well being of a patient such as vitamins, minerals, or herbal based supplements. By "patient" it is meant a human and/or animal such as a mammal or reptile.

In the method of the present invention, a compactable granular mixture is formed containing (i) at least about 3 weight percent of a compaction enhancing therapeutic compound, (ii) at least one other therapeutic compound that is different from the compaction enhancing therapeutic compound and (iii) less than about 15 weight percent of non-aesthetic excipients. The compactable granular mixture is then compressed to form one or more tablets.

The compaction enhancing therapeutic compound is any therapeutic compound that enhances the compactability of the other therapeutic compound. By "enhances the compactability" is meant that when the compaction enhancing therapeutic compound is mixed in the amounts (i.e., at least 3 weight percent) and manner (such as for example granulating, solvent dissolution and removal, or blending) as described herein with the other therapeutic compound, and optional lubricant, the granular mixture formed can be compressed into a tablet having acceptable friability (i.e., about 1% or less), and an increased hardness of at least about 10%, more preferably at least about 20%, and most preferably 50%, based on a tablet of the same weight, shape, and size, compressed under the same conditions, and not containing the compaction enhancing therapeutic compound. Hardness and friability can be determined by those techniques described hereinafter.

Preferably, the amount of compaction enhancing therapeutic compound in the tablet is at least about 3 weight percent to about 99.5 weight percent, more preferably from about 5 weight percent to about 50 weight percent and most preferably from about 5 weight percent to about 15 weight percent, based on the total tablet weight.

Examples of compaction enhancing therapeutic compounds include for example glycosaminoglycans such as heparin, dermatan sulfate, chondroitin, or sulodexide; herbal or botanical based extracts such as St. John's Wort extract, horse chestnut, ginseng, ginko biloba, kelp, grape seed extract; vitamins such as niacinamide ascorbate, and derivatives thereof; salt forms of minerals; anti-inflammatory agents such as naproxen; antibiotics such as cephalosporin; cholesterol lowering agents such as cholestyramine; pharmaceutically acceptable salts of any of the foregoing; or any combination thereof.

In a preferred embodiment of the present invention, the compaction enhancing therapeutic compound is a glycosaminoglycan such as chondroitin, derivatives of chondroitin, including pharmaceutically acceptable salts thereof; an herbal or botanical extract such as St. John's Wort extract, or grape seed extract; or combinations thereof.

The tablet also contains at least one other therapeutic compound that is different from the compaction enhancing therapeutic compound. This other therapeutic compound may be any therapeutic compound known to those skilled in the art. For example, the other therapeutic compound may be a compaction enhancing therapeutic compound as previously described herein, or a compound that does not enhance compaction (i.e., a non-compaction enhancing therapeutic compound).

Examples of therapeutic compounds that may be used as the other therapeutic compound include anti-inflammatory agents; antibiotics; cholesterol lowering agents; antifungal agents; antineoplastic agents; analgesics; hormones; peptides; anticoagulation agents; circulatory drugs; antianginals; antituberculars; antivirals; narcotics; sedatives; diet products; nutritional supplements such as vitamins or minerals; herbal or botanical extracts; anti-smoking libido agents; amino acids, aminosugars; pharmaceutically acceptable salts or derivatives of any of the foregoing; or any combination thereof. Specific examples of vitamins and minerals useful as the other therapeutic compound include Vitamin C, dried powder forms of Vitamin A, Vitamin D, Vitamin E, Vitamin K, or beta carotene; B vitamins, such as thiamin, riboflavin, niacin, Vitamin $B_6$, Vitamin $B_{12}$, biotin, or folic acid; pantothenic acid, calcium, iron, zinc, iodine, magnesium, zinc, selenium, copper, manganese, chromium, molybdenum, potassium, boron, nickel, silicon, tin, vanadium; derivatives or salts of the foregoing; or combinations thereof. Examples of herbal or botanical extracts useful as the other therapeutic compound in the present invention include St. John's Wort extract, horse chestnut, ginseng, ginko biloba, kelp, grape seed extract or combinations thereof.

In a preferred embodiment of the present invention, the other therapeutic compound is a therapeutic compound that does not enhance the compactability of another therapeutic compound. Examples of therapeutic compounds that do not enhance the compactability of a therapeutic compound include for example aminosugars such as glucosamine, including derivatives or pharmaceutically acceptable salts thereof, such as N-acetyl glucosamine sulfate, glucosamine hydrochloride, or glucosamine sulfate; certain vitamins and derivatives or salts thereof such as Vitamin C (e.g., ascorbic acid), Vitamin B (e.g., thiamin hydrochloride, thiamin mononitrate, Vitamin $B_6$, Vitamin $B_{12}$, niacin, biotin, folic acid, pantothenic acid), dried powder forms of Vitamin A, Vitamin D, Vitamin E, Vitamin K, or beta carotene; certain amino acids such as arginine and derivatives thereof or salts thereof; or combinations thereof.

Preferably, the other therapeutic compound is present in the tablet in an amount equal to or less than about 97 weight percent, more preferably from about 0.5 weight percent to about 95 weight percent and most preferably from about 10 weight percent to about 95 weight percent, based on the total tablet weight.

With respect to the compactability properties of a therapeutic compound, one skilled in the art will recognize that a therapeutic compound in one form may enhance the compactability of another therapeutic compound and/or be compactable, but in another form (such as crystalline) may not enhance compactability of a therapeutic compound. As such it is possible that a therapeutic compound in two different forms could be formulated in a single tablet that is substantially free of excipients. However, the tablet should contain at least one therapeutic compound that is chemically different from the compaction enhancing therapeutic compound. For example, the tablet may contain two different compaction enhancing therapeutic compounds and no other therapeutic compounds; one compaction enhancing therapeutic compound and one or more non-compaction enhancing therapeutic compounds; or one or more compaction enhancing therapeutic compound and one or more non-compaction enhancing therapeutic compounds.

The compaction enhancing therapeutic compound and the other therapeutic compound are formed into a compactable granular mixture. By "compactable," it is meant that the granular mixture is capable of forming a 500 mg sized round tablet having a diameter of 7/16" (standard concave) at a compaction pressure of greater than about 1000 lbs and having a hardness of at least about 5 Strong Cobb (SC) and a friability of less than about 1%. Preferably, the compactable granular mixture will be freely flowable for tabletting. Preferably, the compactable granular mixture will have a particle size distribution of 95 percent by weight of the particles passing through a 20 mesh screen and less than 50% by weight of the particles passing through a 100 mesh screen (standard US mesh size).

One skilled in the art will recognize that there are various ways to form a compactable granular mixture. Any method may be used for combining the therapeutic compounds and other desired additives (e.g., excipients) that results in a compactable granular mixture. For example, a compactable granular mixture may be formed by blending the compaction enhancing therapeutic compound, the other therapeutic compound, and any other additive as a dry blend. A compactable granular mixture may also be formed by granulating a mixture containing the compaction enhancing therapeutic compound and other therapeutic compound. A compactable granular mixture may also be formed by at least partially or completely dissolving the compaction enhancing therapeutic compound and other therapeutic compound in a suitable liquid, followed by removal of the liquid. It may also be necessary, as hereinafter described, to subsequently process the mixture formed (e.g. pulverize, agglomerate) after combining the therapeutic compounds to form the compactable granular mixture One skilled in the art will recognize that the desired method chosen for forming a compactable granular mixture will depend upon, for example, the selection of the compaction enhancing therapeutic compound, the other therapeutic compound, and any other desired additive. For example, as explained in further detail hereinafter, it may be necessary, based on the selected therapeutic compounds, to form granules containing an intimate admixture of at least a portion of the compaction enhancing therapeutic compound and at least a portion of the other therapeutic compound to form a compactable granular mixture. However, it may also be possible that certain compaction enhancing therapeutic compounds may simply be mixed with the other therapeutic compound to form a compactable granular mixture.

By "intimate admixture," it is meant that the compaction enhancing therapeutic compound is uniformly admixed at a molecular level with the other therapeutic compound (e.g., in the case of at least partially dissolving both therapeutic compounds in a fluid, and removing the fluid), and/or admixed in a manner so that discrete particles containing the compaction enhancing therapeutic compound or a solid film containing the compaction enhancing therapeutic compound are in at least partial contact with the surfaces of the particles containing the other therapeutic compound. In a preferred embodiment, the compaction enhancing therapeutic compound is at least partially coated as a solid film onto the surfaces of the other therapeutic compound.

There are various ways in which granules containing an intimate admixture of the compaction enhancing therapeutic compound and the other therapeutic compound may be formed. For example, granules of an intimate admixture of the therapeutic compounds may be prepared by wet granulating or solvent dissolution and removal process methods. In some circumstances, dry granulating may be used to form granules containing an intimate admixture of the therapeutic compounds. "Granulating" as used herein refers to a process where two or more smaller particles are combined to form larger granule particles through such processes as extrusion, compaction, fluid-bed granulation, or tumbling. "Solvent dissolution and removal" as used herein refers to a process where solids are at least partially dissolved in a liquid, and then the liquid is removed to form a granular mixture (e.g., spray drying).

One skilled in the art will recognize that there are various ways to wet granulate the therapeutic compounds. Typically, the therapeutic compounds will be mixed in the presence of a granulating fluid, and wet granules containing an intimate admixture of the therapeutic compounds will be formed simultaneously with mixing, and/or subsequently through additional means. The wet granules containing the therapeutic compounds are then preferably dried and pulverized to a suitable particle size for tabletting.

There are various ways in which the granulating fluid may be added to the therapeutic compounds. For example, a dry blend may be formed containing the therapeutic compounds, and the granulating fluid may be added to the dry blend to form a wetted mixture of therapeutic particles. Alternately, one or more compaction enhancing therapeutic compounds may be dissolved or dispersed in the granulating fluid that is then added (e.g., by spraying) to a dry blend containing the other therapeutic compound to form a wetted mixture of therapeutic particles.

One skilled in the art will also recognize that there are various ways in which to granulate the wetted mixture of therapeutic particles. For example, granules may be simultaneously formed while adding the granulating fluid to the therapeutic compound(s) with mixing, such as tumbling, vibrating or shaking. Also, granules may be formed by extruding the wetted mixture of therapeutic granules and/or particles through a die or screen to form larger granules in various shapes such as noodles, pellets, briquettes, spheres, or combinations thereof.

Suitable equipment for wet granulating is disclosed in for example Chemical Engineers' Handbook, by Perry and Chilton, fifth edition, published by McGraw-Hill Inc., 1973, Chapters 8 and 19, the disclosure of which is hereby incorporated by reference in its entirety. In a preferred embodiment of the present invention, continuous granulation equipment is used such as a single screw or twin screw extruder. A preferred extruder is an extructor supplied by Rietz Manufacturing Company. Alternatively, batch equipment designed for the blending both solids and liquids may be used such as for example cone and screw mixers, double arm kneaders, twin blade conical mixers, planetary mixers, helical ribbon blade mixers, conical blenders, or combinations thereof.

The granulating fluid used for wet granulating may be water or any biocompatible solvent that is effective in forming granules containing an intimate admixture of the therapeutic compounds. In a preferred embodiment of the present invention, the granulating fluid is chosen so that the compaction enhancing therapeutic compound is at least partially soluble and more preferably completely soluble in the granulating fluid. Preferably also, the granulating fluid is selected so that the other therapeutic is at least partially insoluble.

The amount of granulating fluid added during granulation to form the wetted mixture of therapeutic particles will depend on such factors as the processing equipment chosen, the types of therapeutic compounds selected, the particle size of the therapeutic compounds, and length of processing time. Typically however the amount of fluid will be from about 5 weight percent to about 30 weight percent, and more preferably from about 8 weight percent to about 15 weight percent, based on the total weight of solids being granulated.

Examples of fluids that may be used include water, biocompatible organic solvents such as $C_1$ to $C_4$ alkyl alcohols, such as methanol, ethanol, n-propanol, isopropanol, or butanol; ethers such as alkoxylated ethers, alkyl ethers, diether, triethers, oligo ethers, polyethers, or cyclic ethers; ketones such as acetone or methyl ethyl ketone; alkyl acetates such as ethyl acetate; alkanes, such as $C_5$ to $C_8$ aliphatic alkanes such as hexane or heptane; cyclic hydrocarbons such as $C_5$ to $C_6$ cyclic hydrocarbons such as cyclopentane or cyclohexane; aromatic hydrocarbons and derivatives thereof such as toluene; or combinations thereof.

It is also possible to form the granulate mixture using a supercritical fluid as the granulating fluid. A supercritical fluid exists at conditions where its liquid and gaseous states are indistinguishable from one another. The critical temperature of a fluid is the temperature above which that fluid cannot be liquified by an increase in pressure. The critical pressure of a fluid is the pressure of the fluid at its critical temperature. Examples of useful supercritical fluids include carbon dioxide, or mixtures of carbon dioxide and aliphatic or cyclic alkanes.

The temperature and pressure at which wet granulation is carried out will depend on the therapeutic compounds and granulating fluid chosen. Preferably, when using water, wet granulation will be carried out at a temperature of from about 22° C. to about 37° C., and more preferably from about 22° C. to about 30° C. Typical granulation pressures through the die range from about atmospheric pressure to several thousand pounds per square inch (psi). In the case of using a supercritical fluid, wet granulation would be carried out at a temperature and pressure at which the fluid exists in a supercritical state.

Following wet granulation, at least a portion of the granulating fluid is removed from the wet granulate mixture to form a dry granulate mixture. The amount of fluid removed will depend on such factors as the total amount of granulating fluid added, selection of the therapeutic compounds, particle sizes of the therapeutic compounds, and the solubilities of the therapeutic compounds in the granulating fluid. Preferably, at least about 50 weight percent, and more preferably from about 80 weight percent to about 98 weight percent of the added granulating fluid in the wet granulate mixture is removed to form a dry granulate mixture. The drying temperature is preferably chosen to efficiently remove the granulating fluid without degrading the therapeutic compounds in the granulate mixture.

A granulate mixture may also be formed by at least partially dissolving, and more preferably completely dissolving the compaction enhancing therapeutic compound and the other therapeutic compound in a liquid, and removing the liquid by any suitable technique to form granules containing the therapeutic compounds in intimate admixture. The selection and amount of liquid used will depend on the solubilities of the therapeutic compounds.

Examples of suitable liquids include water, biocompatible organic solvents such as $C_1$ to $C_4$ alkyl alcohols, such as methanol, ethanol, n-propanol, isopropanol, or butanol; ethers such as alkoxylated ethers, alkyl ethers, diether, triethers, oligo ethers, polyethers, or cyclic ethers; ketones such as acetone or methyl ethyl ketone; alkyl acetates such as ethyl acetate; alkanes, such as $C_5$ to $C_8$ aliphatic alkanes such as hexane or heptane; cyclic hydrocarbons such as $C_5$ to $C_6$ cyclic hydrocarbons such as cyclopentane or cyclohexane; aromatic hydrocarbons and derivatives thereof such as toluene; or combinations thereof.

Any technique known to those skilled in the art for removing the liquid from the therapeutic compound may be used such as continuous dryers (e.g., spray, fluid bed, tube, Witte or tunnel dryers), or batch dryers (e.g., rotary, pan, vacuum, or microwave dryers). In a preferred embodiment, the liquid is removed by a spray dryer. The drying conditions (e.g., temperature and pressure) will depend on the selection of liquid and therapeutic compounds, and should be chosen so as to not degrade the therapeutic compounds.

It is also possible, depending on the compaction enhancing therapeutic compound chosen, and possibly the level of moisture present in the mixture being granulated, that dry granulation can be used to form granules containing an intimate admixture of the compaction enhancing therapeutic compound and other therapeutic compound. "Dry granulation" refers to a granulation process where no external fluid is added during processing. In such an embodiment, preferably the therapeutic compounds being granulated contain a total of at least about 4 wt % moisture, more preferably from about 5 wt % to about 15 wt % moisture, and most preferably from about 6 wt % to about 10 wt % moisture, based on the total weight of the therapeutic compounds. Such moisture is preferably inherently present in the therapeutic compounds as supplied. Preferably, the moisture present is water. It is believed that having some moisture in the therapeutic compounds aids in achieving an intimate admixture during dry granulation.

Any technique known to those skilled in the art may be used for dry granulating that promotes the formation of an intimate admixture of the therapeutic compounds. For example, dry granulation may be accomplished by admixing the compaction enhancing therapeutic compound and other therapeutic compound in a suitable piece of mixing equipment, and/or using compaction equipment, such as a roll press, to compact the dry blend into a desired shape to form an intimate admixture. In a preferred embodiment, dry granulation is carried out using a Chilsonator™ press.

The temperature and pressure at which dry granulation is carried out will depend on the therapeutic compounds chosen. Preferably, dry granulation will be carried out at a temperature of from about ambient to about 45° C., and more preferably from about 20° C. to about 30° C.

Although it is preferred to form granules containing an intimate admixture of the compaction enhancing therapeutic compound and other therapeutic compound, it may be possible to simply blend the therapeutic compounds to form a compactable granular mixture. Any suitable equipment may be used to blend the therapeutic compounds including continuous or batch mixers suitable for mixing solids such as cone and screw mixers, twin blade conical mixers, planetary mixers, helical ribbon blade mixers, conical blenders.

To obtain a freely flowable compactable granular mixture, it may be desirable to further process the mixture containing the compaction enhancing therapeutic compound and other therapeutic compound prior to compressing into tablets. For example, when the therapeutic compounds are combined using wet or dry granulating methods, it may be desirable to further reduce the particle size of the coarse granules (e.g., noodles, pellets) obtained from such methods. Any suitable particle size reduction technique may be used that will provide the desired granulate particle size. Examples of suitable particle size reduction equipment is disclosed in for example Chemical Engineers' Handbook, by Perry and Chilton, fifth edition, published by McGraw-Hill Inc., 1973, Chapter 8, the disclosure of which is incorporated by reference in its entirety. Preferred particle size reduction equipment includes a comil; a Fitz mill manufactured by the Fitzpatrick Company; delumpers; hammer mills or combinations thereof.

In the case of using solvent dissolution and removal techniques as previously described herein (e.g., spray drying), it may be desired to further increase the particle size of the granulate mixture. Any method known to those skilled in the art may be used to further agglomerate the granulate mixture, such as the wet granulation and dry granulation techniques previously described herein. Also, fluid beds, spheronization equipment, or rotating pans may used to agglomerate.

The compactable granular mixture that is compressed may contain low levels of excipients (i.e., additives) as hereinafter described, or other therapeutic compounds, that are added after combining the at least one compaction enhancing therapeutic compound and other therapeutic compound by such techniques as granulation. In a preferred embodiment of the resent invention, at least a portion of the compaction enhancing therapeutic compound is wet granulated with at least a portion of the other therapeutic compound. Preferably, at least 5 eight percent, and more preferably at least 10 weight percent of the compaction enhancing therapeutic compound is granulated with at least 15 weight percent, and more preferably at east 30 weight percent of the other therapeutic compound. The remaining therapeutic compounds may be, for example, simply admixed after granulation.

In a preferred embodiment, the compactable granular mixture is prepared by wet granulating all the compaction enhancing therapeutic compound and all the other therapeutic compound by adding water in a high shear granulator or extractor, and drying the granules formed in a fluid-bed dryer, tunnel dryer, or tray dryer to obtain granules containing from about 0.5 weight percent to about 10 weight percent moisture, based on the total weight of the granules. The granules are then preferably milled through a Fitz mill equipped with a 20 U.S. standard mesh screen.

The compactable granular mixture formed is preferably in a freely flowable form for feeding into compression equipment to form tablets. Preferably, the flow of the compactable granular mixture is from about 5 to about 30 seconds through a funnel having an upper opening diameter of about 8.89 cm, a lower opening of about 1.11 cm, and a height from upper opening to lower opening of about 20.32 cm. Also preferably, the particle size distribution is such that 95 percent by weight of the particles pass through a 20 mesh screen and less than 50% by weight of the particles pass through a 100 mesh screen (standard US mesh size). Also, preferably, any fluids used in forming the compactable granular mixture are removed so that the mixture contains less than about 15 weight percent, more preferably less than about 10 weight percent, and most preferably less than about 8 weight percent moisture based on the total weight of the therapeutic compound.

In addition to the therapeutic compounds, the compactable granular mixture that is compressed to form a tablet may contain additives (i.e., excipients) in an amount of less than about 15 weight percent, based on the total weight of the compactable granular mixture (dry basis). Examples of additives that may be included in the compactable granular mixture are non-therapeutic binding agents, lubricants, diluents, disintegrants, glidants, absorbents, antiadherents, surfactants, coating agents, gelling agents, colorants, flavorants, or combinations thereof. One skilled in the art will recognize that some additives may serve a dual purpose in the tablet composition. For example, many cellulose containing compounds can serve as a binding agent, and diluent or disintegrant at high levels.

The additives may be added in any manner that provides a uniform dispersion of the additives in the compactable granular mixture that is compressed into tablets. For example, the additives may be added to one or more of the therapeutic compounds prior to, or during combining of the therapeutic compounds. For example, the additive may be mixed with the therapeutic compounds to form a dry blend prior to wet granulation or dry granulation. The additive may also be dissolved or dispersed in a liquid containing the therapeutic compounds prior to a solvent dissolution and removal process, or in a granulating fluid, optionally containing the compaction enhancing therapeutic compound prior to wet granulating. In such procedures, the additive is preferably part of the granule particles making up the granulate mixture. The additives may also be added subsequent to forming granules of therapeutic particles provided that the additive is uniformly dispersed in the compactable granular mixture prior to forming the tablet composition. For example, the additive may be blended as is with the granules of therapeutic compounds or may be dissolved or dispersed in a biocompatible liquid and applied to the granules of therapeutic compounds.

The preferred method of adding the additive will depend upon the additive. For example, binding agents,such as polyvinylpyrolidone (PVP) or hydroxypropylmethylcellulose are preferably added prior to, or during the forming of the granules containing the therapeutic compounds, so that the additive is part of the granule formed. Dry binding agents, such as microcrystalline cellulose, are preferably added subsequent to forming granules of the therapeutic compound. Also, for example, non-compaction enhancing therapeutic compounds, such as glucosamine, can be granulated with 5 wt % polyvinylpyrrolidone, and mixed with a compaction enhancing therapeutic compound such as chondroitin that has a moisture content above 7 wt %. Some specific examples of additives useful in the method of the present invention are described below.

In a preferred embodiment of the present invention, the compactable granular mixture may contain less than about 10 weight percent, more preferably less than about 5 weight percent and most preferably from 0 to about 3 weight percent non-therapeutic binding agents based on the total weight of the compactable granular mixture (dry basis). Any binding agent that imparts cohesive strength to granules containing the therapeutic compounds or the compactable granular mixture may be used. Examples of non-therapeutic binding agents useful in the present invention include for example polyvinyl pyrrolidone; modified or unmodified starch; cellulose containing compounds such as hydroxypropyl methylcellulose (HPMC), hydroxypropylcellulose (HPC), carboxymethylcellulose (CMC), methylcellulose or ethylcellulose; polyalkyleneglycols such as polyethyleneglycol or polypropyleneglycol; gelatin; acacia gum; guar gum; sodium alginate; amylopectin, sorbitol; glucose; dextrin or combinations thereof. Preferred binding agents are polyvinyl pyrrolidone, HPMC, lower substituted HPC or combinations thereof.

The compactable granular mixture may also contain one or more lubricants to inhibit sticking of the granules or compactable granular mixture during processing. Preferably, the lubricant is present in the compactable granular mixture in an amount of from 0 weight percent to about 5.0 weight percent, and more preferably from about 0 to about 2.0 weight percent based on the total weight of the compactable granular mixture (dry basis). Examples of suitable lubricants include stearates such as stearic acid, palmitostearate, magnesium stearate, zinc stearate or calcium stearate; talc; hydrogenated vegetable oil; hydrogenated castor oil; liquid paraffin; surfactant; or combinations thereof.

The compactable granular mixture may also contain diluents that increase the bulk of the tablet. Examples of diluents useful in the present invention include for example sugars such as mannitol, sorbitol, or xylitol, lactose, dextrose, fructose, amylose, or sucrose; microcrystalline cellulose; ethyl cellulose; modified or unmodified starch; clays such as kaolin, alkaline earth metal carbonates, phosphates or sulfates such as calcium carbonate, magnesium carbonate, calcium phosphate, (e.g. di and tri basic calcium phosphate), calcium sulfate, or barium sulfate; magnesium trisilicate; aluminum hydroxide; or combinations thereof. The diluents preferably make up from 0 to about 15 weight percent, and more preferably 0 to about 10 weight percent of the compactable granular mixture (dry basis).

Disintegrants are used to facilitate the break-up of the tablet, after the tablet is administered to the patient. Preferably, the compactable granular mixture will contain from 0 to about 5 weight percent and more preferably from about 0.5 weight percent to about 2.0 weight percent disintegrants based on the total weight of the compactable granular mixture (dry basis). Examples of disintegrants useful in the present invention include modified or unmodified starches such as corn starch, potato starch, or wheat starch; croscarmellose, clays; cross-linked polyvinyl pyrrolidone; cellulose containing compounds, gums, algins, surfactant, HPC, or combinations thereof.

Coating agents are applied to the surfaces of the formed tablet and provide, for example, reduced future friability and ease of swallowability. Preferably, the amount coating agent is from about 0.5 wt % to about 6.0 wt % and more preferably from about 1.0 wt % to about 5.0 wt % based on the total weight of the compactable granular mixture (dry basis). Examples of suitable coating agents include cellulose containing compounds such as hydroxypropylmethylcellulose, hydroxypropylcellulose, carboxymethylcellulose, methylcellulose or ethylcellulose; polyalkyleneglycols such as polyethyleneglycol or polypropyleneglycol; or combinations thereof.

The compactable granular mixture may also contain wetting agents, colorants, flavorants or combinations thereof. These additives preferably make-up from about 0.1 weight percent to about 10 weight percent, and more preferably from about 0.3 weight percent to about 5 weight percent of the compactable granular mixture (dry basis). Examples of suitable wetting agents include sodium dodecyl sulphate, sodium lauryl sulphate, polyoxyethylene sorbitan fatty acid esters (e.g., Tween™ compounds), polyoxyethylene stearates, sorbitan fatty acid esters or combinations thereof. Suitable colorants include for example red beet powder, ferric oxides, FD & C dyes or combinations thereof. Flavoring agents useful in the present invention include for example fruit flavors, or sweeteners such as sodium saccharin, aspartame, confectionary sugar, sorbitol, sucrose, xylitol, or combinations thereof.

The compactable granular mixture thus prepared in accordance with the method of the present invention is compressed into a tablet according to any technique known to those skilled in the art. For example, in compacting the compactable granular mixture, the compactable granular mixture can be added to a die, and compressed into a tablet having the desired shape and weight. Prior to adding the compactable granular mixture to the die, it may be desirable to apply an external lubricant to the wall of the die. Examples of external lubricants useful in the method of the present invention include talc; starch; stearates such as magnesium stearate; hydrogenated vegetable oil; surfactant or combinations thereof Preferably the compactable granular mixture is compressed at any suitable pressure and temperature to form a tablet having the desired properties such as strength, hardness, disintegration and release of the therapeutic compounds upon administration. Preferably, the compaction conditions are such that there is no degradation of the therapeutic compounds. Also, preferably, the compaction conditions are below the melting points of the therapeutic compounds to prevent lower tablet hardness or other tabletting process problems (e.g. glazing). Typical compaction pressures range from about 1000 lbs to about 10,000 lbs, and more preferably from about 4,000 lbs to about 8,000 lbs, where lbs is pounds force. Typical compaction temperatures range from about 15° C. to about 60° C. and more preferably from about 20° C. to about 40° C.

The tablets thus produced may be further processed as desired. For example, the tablet may be coated according to any technique known to those skilled in the art. Suitable coatings include those compounds previously described as being useful as coating agents for the compactable granular mixture. The tablets may also be enteric or regularly polished with such compounds as Carnuba wax.

The tablet compositions useful in the present invention contain preferably from about 3 weight percent to about 99.5 weight percent, more preferably from about 5 weight percent to about 50 weight percent, and most preferably from about 5 weight percent to about 15 weight percent of at least one compaction enhancing therapeutic compound, based on the total weight of the tablet composition. The tablets also preferably contain from about 0.5 weight percent to about 97 weight percent, more preferably from about 10 weight percent to about 95 weight percent, and most preferably from about 40 weight percent to about 95 weight percent of at least one second therapeutic compound that is different from the compaction enhancing therapeutic compound, based on the total weight of the tablet composition. The compaction enhancing therapeutic compound is preferably in intimate admixture with the second therapeutic compound. More preferably, the compaction enhancing therapeutic compound at least partially coats particles of the second therapeutic compound.

The tablet composition thus produced also preferably contains less than about 15 weight percent, more preferably less than about 8 weight percent, and most preferably less than about 2 weight percent excipients, based on the total weight of the tablet composition (dry basis). The excipients may be any of the additives previously described herein that are present in the compactable granular mixture and in the amounts previously described for the compactable granular mixture. Preferably, excipients that serve as a lubricant are present in the tablet composition in an amount of no more than 0.5 weight percent based on the total weight of the tablet composition.

The overall weight of the tablet ranges from about 100 mg to about 2000 mg, and more preferably from about 450 mg to about 1600 mg.

One skilled in the art will recognize that the tablet compositions made in accordance with the methods of the present invention can be used for a variety of purposes. For example, the tablets may be formulated to provide treatment of connective tissue, such as to prevent, repair, or lessen ailments of the joints and cartilage tissue, such as observed with arthritis. The tablet compositions may also be prepared to treat ailments of the skin such as hardening, roughening, aging, or wrinkling of the skin. The tablet compositions may also be prepared to provide to a patient nutritional supplements of vitamins, minerals, antioxidants, or to function as an appetite suppressant, analgesic, anti-smoking libido, or combinations thereof. The tablet compositions may also be prepared to enhance the emotional well being of a patient through for example herbal based extracts. The tablet compositions of the present invention may also be prepared to treat ailments such as viral, fungal, or bacterial infections, diseases, or injuries to the body.

There are many advantages to the tablet compositions prepared in accordance with the methods of the present invention. For example, by the tablet compositions being substantially free of excipients, smaller (in weight and volume) tablets can be prepared containing the same amount of therapeutic compound. By decreasing the excipients present in the tablet, the tablets prepared according to the method of the present invention can be more easily ingested, and/or formulated to contain more therapeutic compound(s) in a single tablet. By being able to increase the amount of therapeutic compounds in a single tablet, one reduces the need to ingest multiple tablets at a single time and/or multiple doses of the same product. Additionally, the reduction of excipients in tablets is beneficial to hyper-allergenic patients and also has a very positive effect on diurnal consumer compliance.

In a preferred embodiment of the present invention, the tablet composition made in accordance with the methods of the present invention contains from about weight percent 3 to about 80 weight percent, and more preferably from about 30 to about 60 weight percent of at least one glycosaminoglycan; from about 3 weight percent to about 95 weight percent, and more preferably from about 5 weight percent to about 70 weight percent of at least one amino sugar; and less than about 2 weight percent, and more preferably less than about 0.5 weight percent of excipients based on the total weight of the tablet (dry basis). Preferably, the amino sugar is glucosamine, or a derivative or pharmaceutically acceptable salt thereof and the glycosaminoglycan is chondroitin or a derivative or pharmaceutically acceptable salt thereof.

In this preferred embodiment, other therapeutic compounds may be present in the tablet composition such as manganese ascorbate, sodium ascorbate, calcium ascorbate, Vitamin C (i.e., ascorbic acid), dried powder forms of Vitamin A, Vitamin D, Vitamin E, Vitamin K, or beta carotene; vitamin $B_6$, niacin, phosphorous containing salts, zinc containing salts, copper containing salts, calcium containing salts such as calcium citrate, calcium carbonate, oyster shell, magnesium, manganese sulfate, boron, estrogen(s), or combinations thereof. Preferably calcium is present in an amount of from about 7 weight percent to about weight percent; and the vitamin C is preferably present in an amount of from about 1 weight percent to about 10 weight percent, based on the total weight of the tablet composition (dry basis).

Also preferably in this embodiment, the overall weight of the tablet ranges from about 100 mg to about 2000 mg, and more preferably from about 500 mg to about 2000 mg. The aminosugar is preferably present in an amount of from about 250 mg to about 1000 mg, and the glycosaminoglycan is preferably present in an amount of from about 200 mg to about 1000 mg. Any excipients are preferably present in an amount of less than about 50 mg.

The above preferred tablet composition containing an aminosugar and glycosaminoglycan is particularly useful for the treatment of connective tissues. Other preferred compositions that can be formed into a tablet in accordance with the method of the present invention are those compositions disclosed in for example U.S. Pat. Nos. 5,364,845 and 5,587,363 both to Henderson, the disclosures of which are hereby incorporated by reference in their entireties.

EXAMPLES

Some embodiments of the present invention will now be described in detail in the following Examples. Tablet compositions were prepared in accordance with the method of the present invention and evaluated for various properties. The following test procedures were used in the Examples for evaluating tablet properties.

TABLE 1

Test Methods for Properties Measured and Abbreviations Used in Examples

| Property | Units | Method | Equipment |
|---|---|---|---|
| Hardness | Strong-Cobb | — | Key International Hardness Tester |
| Disintegration Time (DT) | Minutes (min) | USP[1] 2040 | VanderCamp - disintegration Apparatus |
| Ejection Force (EJ Force) | Pounds (lbs) | — | $B_3B$ 16 station Instrumented Tablet Press |
| Weight variation (Wt. Var.) | % | USP 2091 | Mettler 3 place balance |
| Friability (Friab.) | % | USP 1216 | Tablet Friability Apparatus |

[1]USP refers to the United States Pharmacopea, Vol. USP XXIV/NF XIX, published by U.S. Pharmacopea Convention Incorporated located in Rockville, MD, 1999, The number following "USP" refers to the section in which the test method is found.

In Table 1 above, weight variation is expressed as the percent standard deviation in tablet weight for 20 tablets based on the average tablet weight. Friability is expressed as the percent of the tablet weight loss that was friable in the friabilitator after 100 rotations (20 tablets).

Unless otherwise indicated in the Examples, the chondroitin used was chondroitin sulfate sodium salt obtained from Tomen America located in New York, N.Y. The chondroitin had an active ingredient content of 85 weight percent, and loss on drying (LOD) of 9.25 weight percent based on the total weight. Unless otherwise indicated in the Examples, the glucosamine used was glucosamine HCl obtained from Nutratech Corp., located in Fairfield, N.J. The glucosamine had an active ingredient content of 99 weight percent and was milled prior to use in a Fitz mill having a 60 mesh screen. Magnesium stearate was obtained from Mallinkrodt located in St. Louis, Mo. Any reference in the examples to mesh screen size refers to U.S. standard mesh size.

Comparative Example 1

Tablets containing 470.59 mg of chondroitin, 505.05 mg glucosamine and 4.90 mg of magnesium stearate were prepared using either milled glucosamine as previously described or unmilled glucosamine. The unmilled glucosamine had a particle size distribution of 95 wt % of the particles being smaller than a 20 mesh screen size, and 50 wt % of the particles being greater than a 60 mesh screen size.

The tablets were prepared by mixing the proper amounts of chondroitin and glucosamine in a blender for 15 minutes to form a dry blend. The magnesium stearate was separately mixed with an equal amount of the dry blend and passed through a 30 mesh screen to form a magnesium stearate mixture. This magnesium stearate mixture was then added to the dry blend and mixed for an additional 5 minutes. Tablets were then prepared using a Manesty 16 station $B_3B$ instrument equipped with an instrumentation package, supplied by SMI Corp., capable of continuously recording compression speed, compression force, and ejection force.

The tabletting conditions were as follows:

| | |
|---|---|
| Tabletting speed | 40 revolutions per minute (RPM) |
| Compression force | varied |
| Tablet punches | 5/16" × 3/4" caplet, B tooling |
| Tablet weight | 989.24 mg |

For tablets prepared using milled glucosamine, a tablet hardness of 10 Strong-Cobb was achieved at a compaction pressure of 5500 lbs. For tablets prepared using unmilled glucosamine a hardness of 1.5 Strong-Cobb was obtained at a compaction pressure of 3000 lbs. For both tablets, at a compaction pressure of 4000 lbs and greater, capping was observed.

Comparative Example 2

To a blender was added 470.59 parts by weight chondroitin, 505.05 parts by weight glucosamine, and 35.35 parts by weight red beet powder to form a dry blend. This dry blend was mixed for 15 minutes and then dry granulated in a chilsonator supplied by Fitzpatrick located in South Hackensack, N.J. to form large granules. The resulting granules were then fed into a Fitz mill having a 60 mesh screen size to form chondroitin/glucosamine granules. The chondroitin/glucosamine granules were then passed though a Sweco supplied by Sweco Inc. located in Florence, Ky. to collect particles between 20 mesh and 100 mesh particle size for tabletting. Oversized particles were recycled back to the Fitz mill and undersized particles were recycled back to the chilsonator.

The chondroitin/glucosamine granules thus obtained were tabletted by preparing a magnesium stearate mixture containing 3.81 parts magnesium stearate and 3.81 parts chondroitin/glucosamine granules and passing this mixture through a 30 mesh screen. The magnesium stearate mixture and the remaining chondroitin/glucosamine granules were then blended for five minutes. The resulting mixture was then tabletted in accordance with the procedure described in Comparative Example 1 (target tablet weight 975.64 mg). It was found that capping was observed at a compaction pressure of 3000 lbs and tablets could not be formed.

Example 3

Tablets containing 470.59 mg of chondroitin, 526.35 mg of polyvinylpyrolidone (PVP) granulated glucosamine, and 3.75 mg of magnesium stearate were prepared. The PVP granulated glucosamine contained 93 weight percent glucosamine and 5 wt % PVP and was obtained from Nutratech Corp., located in Fairfield, N.J. Tablets were prepared according to the procedure described for Comparative Example 1. The tablets were evaluated for disintegration time, hardness, and friability. The results are shown below in Table 2:

TABLE 2

Tablet Performance Using PVP Granulated Glucosamine

| Property | Measured Value |
|---|---|
| Disintegration Time, minutes | 18.5 (compressed at 7000 lbs) |
| Hardness, Strong-Cobb (SC) | |
| Compressed at 4000 pound | 7.6 |
| Compressed at 7000 pound | 17.2 |

TABLE 2-continued

Tablet Performance Using PVP Granulated Glucosamine

| Property | Measured Value |
| --- | --- |
| Compressed at 9000 pound | 22.8 |
| Friability, wt % loss | 0.01% (compressed at 7000 lbs) |
| Weight Variation, % standard deviation | 2.82% (compressed at 7000 lbs) |

In a separate experiment, the PVP granulated glucosamine was compressed at various pressures with no chondroitin. The PVP granulated glucosamine did not compress into a tablet indicating that the chondroitin was acting to enhance the compactability of the PVP granulated glucosamine.

Examples 4 to 17

In Examples 4 to 17 tablets were prepared as described below where the following parameters were varied:

(a) particle size of a compaction enhancing therapeutic compound (chondroitin, particles ranging in size ranges between (i) 20 and 80 mesh, (ii) between 80 and 200 mesh, and (iii) through 200 mesh, (where the greater the mesh size, the smaller the particle size);

(b) moisture level of granulate mixture (10 wt %, 7 wt %, and less than 4 wt % moisture, based on the total weight of the granulate mixture); and (c) amount of lubricant in tablet (0.1 wt %, 0.55 wt %, and 1.0 wt %, based on the total weight of the granulate mixture).

To an appropriately sized Hobart type blender was added 1882 parts by weight of chondroitin having one of the particle size ranges described above, 2020 parts by weight of glucosamine, and magnesium stearate, as a lubricant, at one of the levels described above to form a dry blend. This dry blend was granulated by gradually adding 500 parts by weight water at ambient temperature while mixing until granules were formed. This wet granulate mixture was then dried in an oven at 70° C. until the target moisture level (indicated in Table 2) in the granulate mixture was achieved. After drying, the granulate mixture was milled in an oscillator, supplied by Erweka, located in Heusenstamm, Germany using a 20 mesh screen.

The granulate mixtures produced were tabletted on a Manesty 16 station $B_3B$ instrument equipped with an instrumentation package, supplied by SMI Corp., capable of continuously recording compression speed, compression force, and ejection force.

The tabletting conditions were as follows:

| | |
| --- | --- |
| Tabletting speed | 40 revolutions per minute (RPM) |
| Compression force | 7000 lbs. |
| Tablet punches | 5/16" × 3/4" caplet, B tooling |
| Tablet weight | 1.085 gms. |

The tablet compositions produced were measured for hardness, friability, disintegration time, ejection force, and weight variation according to the aforementioned test procedures.

A summary of the properties measured for each tablet composition prepared is shown below in Table 3. The values for ejection forces are based on the average of four punches, which were based on 5 revolutions.

TABLE 3

Measured Properties of Tablet Compositions Prepared

| Ex. | $H_2O$ (wt %) | Lub. (wt %) | Part. Size (mesh) | Hardness (Strong-Cobb) | DT (min) | EJ Force (lbs) | Wt. Var. (%) | Friab. (%) |
| --- | --- | --- | --- | --- | --- | --- | --- | --- |
| 4 | 7.0 | 0.55 | 80–200 | 25.7 | 22.5 | 70 | 1.986 | .06 |
| 5 | 7.0 | 1.0 | 20–80 | 15.6 | 25.5 | 57 | 2.106 | .19 |
| 6 | 7.0 | 0.55 | 80–200 | 24 | 25 | 68 | 2.196 | .08 |
| 7 | 7.0 | 0.1 | through 200 | 36.5 | 20.5 | 181 | 1.785 | .05 |
| 8 | 4.0 | 0.1 | 80–200 | 16.1 | 23.5 | 98 | 0.685 | .1 |
| 9 | 10.0 | 0.1 | 80–200 | 41.1 | 21.5 | 123 | 0.81 | .06 |
| 10 | 7.0 | 0.1 | 20–80 | 24.3 | 25 | 129 | 2.027 | .08 |
| 11 | 7.0 | 0.55 | 80–200 | 23.7 | 23.5 | 66 | 2.252 | .07 |
| 12 | 4.0 | 1.0 | 80–200 | 14.8 | 20.5 | 97 | 2.377 | .3 |
| 13 | 4.0 | 0.55 | through 200 | 16.5 | 21.5 | 106 | 2.27 | .1 |
| 14 | 7.0 | 1.0 | through 200 | 28.2 | 24.5 | 54 | 1.391 | .07 |
| 15 | 10.0 | 0.55 | through 200 | 35.1 | 23 | 20.4 | 1.626 | .07 |
| 16 | 10.0 | 1.0 | 80–200 | 0 | 26 | 17.7 | 1.94 | .14 |
| 17 | 10.0 | 0.55 | 20–80 | 24.8 | 20.5 | 26 | 2.165 | .15 |

The results in Table 3 show that the method of the present invention produces tablets that are substantially free of excipients having superior properties. The results show that tablets can be formed from compaction enhancing therapeutic compounds having various particle sizes (column labeled "Part. Size"), lubricant content (column labeled "Lub."), and tablet moisture content (column labeled $H_2O$). A preferred tablet moisture is around 6.0 to 9.0 weight percent based on an analysis of the above data.

Examples 18 to 23

Tablets containing double dosage strength (label claim of 400 mg chondroitin, 500 mg glucosamine) or triple dosage strength (label claim of 600 mg chondroitin, 750 mg glucosamine) of chondroitin and glucosamine were prepared according to the following procedure. A granulate mixture was prepared by mixing for 15 minutes in a planetary blender, a dry blend of 1882.36 grams of chondroitin and 2020.20 grams of glucosamine. Following mixing, 400 grams of purified water was gradually added to the blender with mixing. Following addition of the water, the wet mixture was mixed for an additional time to produce wet granules. The wet granules were then dried in an oven at a temperature of 70° C. until a moisture level of 8.4 wt % was achieved, based on the total weight of the chondroitin/glucosamine granules. The chondroitin/glucosamine dry granules obtained were passed through an oscillator as described in the procedure for Examples 4 to 17.

Tabletting mixtures were prepared, as described below, to achieve upon compaction, (a) a double strength caplet (label claim 400 mg chondroitin and 500 mg glucosamine) containing 975.64 mg of the chondroitin/glucosamine dry granules and 3.81 mg of the magnesium stearate, and (b) a triple strength caplet (label claim 600 mg chondroitin and 750 mg glucosamine) containing 1463.46 mg of the chondroitin/glucosamine dry granules and 5.72 mg of the magnesium stearate. The tabletting mixtures were prepared by mixing the desired amount of magnesium stearate (lubricant) with an approximately equal amount by weight of the dried chondroitin/glucosamine granules having a particle size of less than 30 mesh in a blender. This mixture was then passed through a 30 mesh screen. This screened mixture was added to the dried chondroitin/glucosamine granules in the blender, and mixed for an additional 5 minutes to produce the desired tabletting mixture. The tabletting mixture was then formed into caplets in accordance with the procedure used in Examples 4 to 17 except that the compaction pressure was varied as shown in Table 4 below. The resulting caplets were measured for hardness, disintegration time, weight variation, and friability. The results are reported below in Table 4.

TABLE 4

Properties of Caplets for Examples 4 to 23

| Ex. | Dosage Strength | Compaction Pressure (lbs) | Hardness (Strong-Cobb) | DT (min) | Wt. Var. (%) | Friab. (%) |
|---|---|---|---|---|---|---|
| 18 | Double | 4000 | 13.7 | — | — | — |
| 19 | Double | 7000 | 25.6 | 19 | 1.05 | 0.09 |
| 20 | Double | 9000 | 30.4 | — | — | — |
| 21 | Triple | 4000 | 37.7 | — | — | — |
| 22 | Triple | 7000 | >45 | 28.5 | 0.96 | 0.10 |
| 23 | Triple | 9000 | >45 | — | — | — |

The data in Table 4 shows that the method of the present invention produces tablets that are substantially free of excipients having suitable properties such as compressibility, tablet weight variability, disintegration, and friability. Another advantage of using the present invention under the above conditions was that no capping was observed, even at compression forces up to 9000 pounds.

Examples 24 to 29

Tablet compositions were prepared according to the methods of the present invention using low amounts of a disintegrating agent. The tablets prepared contained 98.62 wt % chondroitin/glucosamine granules prepared in accordance with Examples 18 to 23, 1 wt % Croscarmellose Sodium, supplied by Blanver Farmoquimica Ltda., located in Brazil, and 0.38 wt % magnesium stearate. Also, double strength tablets containing 99.62 wt % chondroitin/glucosamine and 0.38 wt % magnesium stearate were prepared according to the procedure described in Examples 18 to 23.

The tablets containing the disintegrant were prepared by mixing in a blender for 10 minutes, the proper amounts of croscarmellose sodium and chondroitin/glucosamine granules to form a tabletting mixture. The proper amount of magnesium stearate was separately mixed with an equal amount, by weight, of the tabletting mixture that had been passed through a 30 mesh screen. The magnesium stearate mixture was then passed though a 30 mesh screen. The magnesium stearate mixture was then added to the blender containing the tabletting mixture and mixed for 5 minutes. This mixture was then compressed into tablets at various compaction pressures according to the procedure described in Examples 4 to 17.

The resulting tablets were then evaluated for hardness, disintegration time, friability, and weight variation.

The results are shown in Table 5 below:

TABLE 5

Properties of Tablets of Examples 24 to 29

| Ex. | Distintegrant (wt%) | Compaction Pressure (lbs) | Hardness (Strong-Cobb) | DT (min) | Wt. Var. (%) | Friab. (%) |
|---|---|---|---|---|---|---|
| 24 | 0 | 4000 | 13.7 | 19 | 0.93 | 0.19 |
| 25 | 0 | 7000 | 25.6 | 18.5 | 1.09 | 0.091 |
| 26 | 0 | 9000 | 30.4 | 19.5 | 0.89 | 0.083 |
| 27 | 1 | 4000 | 14.0 | 17.5 | 0.79 | 0.21 |
| 28 | 1 | 7000 | 25.3 | 19 | 0.95 | 0.10 |
| 29 | 1 | 9000 | 30.1 | 18.5 | 0.73 | 0.082 |

The results in Table 5 show that the method of the present invention produces tablets having acceptable disintegration properties with and without the use of a disintegrant. The tablets also had acceptable hardness, friability and weight variability.

Examples 30 to 32

To a planetary blender was added 106.33 grams of chondroitin and 2020 grams of glucosamine. This mixture was mixed for 15 minutes in the blender to form a dry blend. This dry blend was granulated by gradually adding 200 grams of purified water at ambient temperature while mixing until granules were formed. This wet granulate mixture was then dried in an oven at 70° C. until a moisture level 1.50 wt % in the granulate mixture was achieved. After drying, the granulate mixture was passed through an oscillator according to Examples 4 to 17. To produce granules containing 5 wt % chondroitin and 95 wt % glucosamine.

Tablets were prepared by mixing in a blender for 15 minutes, 2126.53 grams of the chondroitin/glucosamine granules (containing 5 wt % chondroitin), and 1776.03 grams of chondroitin to form a tabletting mixture. The proper amount of magnesium stearate was separately mixed with an equal amount, by weight, of the tabletting mixture that had been passed through a 30 mesh screen. The magnesium stearate mixture was then passed though a 30 mesh screen. The magnesium stearate mixture was then added to the blender containing the tabletting mixture and mixed for 5 minutes. This mixture was then compressed into tablets at various compaction pressures according to the procedure described in Examples 4 to 17.

The resulting tablets were then evaluated for hardness, disintegration time, and weight variation. A summary of the properties measured for each tablet prepared is shown below in Table 6

TABLE 6

Properties of Tablets Formed from 5 wt % Chondroitin Granules

| Ex. | Compaction Pressure (lbs) | Hardness (Strong-Cobb) | DT (min) | Wt. Var. (%) |
|---|---|---|---|---|
| 30 | 4000 | 13.7 | 18.5 | 1.09 |
| 31 | 7000 | 23.5 | 19 | 0.71 |
| 32 | 9000 | 33.6 | 19.5 | 0.71 |

The data in Table 6 shows that suitable tablets can be formed from granules containing 5 wt % of chondroitin and 95 wt % glucosamine, ungranulated chondroitin, and magnesium stearate. Based on the results of Example 3, using 5 wt % PVP/glucosamine granules, chondroitin appears to be a more effective compacting agent for glucosamine. This is a surprising result considering that PVP is commonly used as a binder for chondroitin and glucosamine tablets.

Examples 33 to 44

Tablets containing 500 mg glucosamine, 400 mg chondroitin, 20 mg Vitamin C, 133 IU Vitamin D and 167 mg calcium were prepared by using (a) ungranulated glucosamine and chondroitin, (b) glucosamine granulated with 5 wt % chondroitin, and (c) fully granulated glucosamine and chondroitin. Three different tablet compositions were prepared as shown in Table 7 below:

TABLE 7

Tablet Compositions for Examples 33 to 44

| Ingredients | A (Ungranulated, mg) | B (5 wt % Granulated, mg) | C (Fully Granulated, mg) |
|---|---|---|---|
| Chondroitin, 85% | 470.59 | 444.01 | 0.0 |
| Glucosamine, 99 wt % | 505.05 | 0.0 | 0.0 |
| 5 wt % granulated chondroitin/glucosamine | 0.0 | 531.63 | 0.0 |
| fully granulated chondroitin/glucosamine | 0.0 | 0.0 | 975.64 |
| Vitamin C-90 | 25.82 | 25.82 | 25.82 |
| Vitamin D | 1.84 | 1.84 | 1.84 |
| Calcium Carbonate DC | 473.13 | 473.13 | 473.13 |
| Magnesium Stearate | 7.50 | 7.50 | 7.50 |
| Total | 1483.93 | 1483.93 | 1483.93 |

The chondroitin/glucosamine granules containing 5 weight percent chondroitin, were prepared according to the procedure used in Examples 30 to 32, except that the wet granules were dried to a LOD content of 1.5 weight percent. The fully granulated chondroitin/glucosamine granules were prepared according to the procedure used in Examples 18 to 23, except that the wet granules were dried to a LOD content of 6.5 weight percent.

Tablets were prepared by mixing Vitamins C-90 and D in a blender for 10 minutes to form a vitamin mixture. Also, magnesium stearate and an equal amount, by weight, of the calcium carbonate were mixed separately and passed through a 30-mesh screen. To an appropriately sized blender was added the vitamin mixture, the remaining calcium carbonate, and the glucosamine and chondroitin (granulated or ungranulated as specified in Table 7 above). This mixture was blended for 10 minutes after which the magnesium stearate mixture was added and blended for 5 more minutes. The resulting tabletting mixtures were tabletted according to the procedure in Examples 4 to 17 at various pressures. The results are shown below in Table 8.

TABLE 8

Performance of Tablet Compostions A through C

| Ex. | Tablet Composition | Compaction Pressure (lbs) | Hardness (Strong-Cobb) | DT (min) | Wt. Var. (%) | Friab. (%) |
|---|---|---|---|---|---|---|
| 33 | A | 4000 | 10.2 | 15 | 2.61 | 6.34 |
| 34 | A | 6000 | 17.1 | 19 | 2.14 | 1.10 |
| 35 | A | 8000 | 26.7 | 21 | 1.78 | capped |
| 36 | A | 9000 | 27.2 | 21.5 | 2.32 | capped |
| 37 | B | 4000 | 19.0 | 18.5 | 0.90 | 0.23 |
| 38 | B | 6000 | 30.8 | 21.5 | 0.56 | 0.06 |
| 39 | B | 8000 | 40.2 | 24 | 0.61 | 0.02 |
| 40 | B | 9000 | >45 | 24.5 | 0.92 | 0.01 |
| 41 | C | 4000 | 20.7 | 23 | 1.05 | 0.22 |
| 42 | C | 6000 | 33.5 | 27.5 | 0.76 | 0.08 |
| 43 | C | 8000 | 42.2 | 29.5 | 0.66 | 0.07 |
| 44 | C | 9000 | >45 | 29 | 0.69 | 0.06 |

For compositions containing the ungranulated glucosamine and chondroitin (i.e., composition A), the tablets could be compressed up to 6000 pounds without capping. For compositions containing glucosamine granulated with chondroitin (i.e., compositions B and C), the addition of other therapeutic compounds in the tablet did not hinder the performance properties of the tablet.

Examples 45 to 48

Tablets containing Vitamin C (i.e., ascorbic acid) and chondroitin were prepared using Vitamin C as is (ungranulated) and Vitamin C granulated with 5 wt % chondroitin (as a compaction enhancing therapeutic compound). Two different tablet compositions were prepared as shown in Table 9 below:

TABLE 9

Tablet Compositions for Examples 45 to 48 (500 mg Vitamin C label claim)

| Ingredients | D (Ungranulated, mg) | E (5 wt % Granulated, mg) |
|---|---|---|
| Chondroitin, 85% | 27.63 | 0.0 |
| Ascorbic acid fine powder | 525 | 0.0 |
| 5 wt % granulated chondroitin/ascorbic acid | 0.0 | 552.63 |
| Microcrystalline cellulose | 22.76 | 22.76 |
| Stearic acid | 5.74 | 5.74 |
| Magnesium stearate | 7.50 | 7.50 |
| Total | 582.02 | 582.02 |

The chondroitin/ascorbic acid granules were prepared by mixing in a blender for 10 minutes, the appropriate amounts of chondroitin and ascorbic acid to form granules containing 5 wt % chondroitin and 95 wt % ascorbic acid. Following mixing, water was gradually added with mixing until uniform granules were formed and the mixture was free of loose powder. The granules produced were dried at 75° C. until the moisture content of the granules was less than 0.2 wt %. The dried granules were passed through an oscillator equipped with a 20 mesh screen according to the procedure in Examples 4 to 17.

To form the tabletting mixtures, ascorbic acid (granulated or ungranulated) and chondroitin (if ungranulated) were mixed in a blender for 10 minutes. A mixture of stearic acid, magnesium stearate, and an equal amount by weight of microcrystalline cellulose (based on the combined weight of the stearic acid and magnesium stearate) was mixed separately in a blender for 2 minutes and passed through a 20 mesh screen. The magnesium stearate mixture was then added to the blender containing the ascorbic acid and chondroitin, and mixed for an additional 5 minutes. The tabletting mixtures were then compressed according to the procedure described in Examples 4 to 17 at various pressures. The results are shown below in Table 10.

TABLE 10

Tablet Performance for Examples 45 to 48

| Ex. | Tablet Composition | Compaction Pressure (lbs) | Hardness (Strong-Cobb) | DT Time (min) | Wt. Var. (%) | Friab. (%) |
|---|---|---|---|---|---|---|
| 45 | D | 2000 | — | — | — | capping |
| 46 | E | 4000 | 8.6 | 5.5 | 0.68 | 0.66 |
| 47 | E | 5000 | 8.9 | 6 | 0.66 | capped |
| 48 | E | 6000 | 8.0 | 6.5 | 0.32 | capped |

The results in Table 10 show that when chondroitin is granulated with ascorbic acid, the compactability of the ascorbic acid can be significantly improved in comparison to simply admixing the ascorbic acid with the chondroitin.

Examples 49 to 50

Grape seed extract was evaluated for its ability to act as a compaction enhancing therapeutic compound for L-arginine HCl. The following procedure was used for preparing granules of grape seed extract and L-arginine.

To a Hobart blender was added 900 grams of L-Arginine HCl. A granulating fluid was prepared by dispersing 100 grams of grape seed extract (90 wt % polyphenols) in 150 grams of isopropanol. To the isopropanol/grape seed extract mixture was added with stirring 100 grams of water in three equal additions (i.e., about 33.3 grams each). The granulating fluid was then added to the L-arginine with mixing to form granules. The granules were then dried in an oven at 50° C. until the moisture in the granules was 1.2 wt %. The dried granules were then passed through an oscillator according to the procedure used in Examples 4 to 17.

Tabletting mixtures were prepared using (a) ungranulated grape seed extract and arginine and (b) granulated grape seed extract and arginine prepared as described above. The compositions of the tabletting mixtures (in weight per tablet) are shown in Table 11.

TABLE 11

Tablet Compositions Containing Grape Seed Extract and L-Arginine HCl

| Ingredients | F (Ungranulated, mg) | G (Granulated, mg) |
|---|---|---|
| Grape Seed/Arginine granules | 0.0 | 267 |
| L-Arginine HCl | 240 | 0.0 |
| Grape seed extract (90 wt % polyphenols) | 27 | 0.0 |
| Magnesium stearate | 3.0 | 3.0 |
| Total | 270 | 270 |

To form the tabletting mixtures, the magnesium stearate was separately mixed with an equal amount by weight of either the grape seed extract/arginine granules (composition G) or a blend of the grape seed extract and L-arginine (composition F) that had been passed through a 30 mesh screen. To this magnesium stearate mixture was added the remaining amount of the grape seed extract and arginine HCl in the appropriate granulated or ungranulated form. These ingredients were then mixed for 2 minutes. The tabletting mixtures were then compressed according to the procedure described in Examples 4 to 17 at various pressures, except that ⅜" SC punches were used. The results are shown below in Table 12.

TABLE 12

Tablet Performance of Tablets Containing Grape Seed Extract and L-Arginine HCl

| Ex. | Tablet Composition | Hardness (Strong-Cobb) | DT Time (min) | Friab. (%) |
|---|---|---|---|---|
| 49 | F | — | — | — |
| 50 | G | 7.2 | 4 | 0.90 |

The results in Table 12 show that when grape seed extract is granulated with L-arginine a tabletting mixture is formed that can be tabletted. The ungranulated grape seed extract and L-Arginine could not be formed into a tablet under the same conditions used to form a tablet from the grape seed extract/arginine granules.

There have thus been described certain preferred embodiments of the present invention. While preferred embodiments have been disclosed and described, it will be recognized by those with skill in the art that variations and modifications are within the true spirit and scope of the invention. The appended claims are intended to cover all such variations and modifications.

What is claimed is:

1. A method of making a tablet composition comprising the steps of:
    (a) forming a compactable granular mixture comprising (i) at least about 3 weight percent of a compaction enhancing therapeutic compound, (ii) at least one other therapeutic compound that is different from the compaction enhancing therapeutic compound and (iii) less than about 15 weight percent of non-aesthetic excipients; and
    (b) compressing the granular mixture to form one or more tablets.

2. The method of claim 1 wherein the compactable granular mixture comprises an intimate admixture of granules, the granules comprising at least a portion of the compaction enhancing therapeutic compound and at least a portion of the other therapeutic compound.

3. The method of claim 2 wherein the compactable granular mixture is formed by the steps comprising wet granulating the therapeutic compounds in the presence of a granulating fluid to form a wet granular mixture, removing at least a portion of the fluid from the wet granular mixture; and reducing the particle size of the granular mixture prior to the compressing.

4. The method of claim 3 wherein the step of wet granulating comprises forming a dry blend comprising the other therapeutic compound and applying the granulating fluid to the dry blend, wherein the compaction enhancing therapeutic compound is present in the granulating fluid, the dry blend, or both.

5. The method of claim 3 wherein the granulating fluid is selected from the group consisting of water, an organic solvent, a supercritical fluid or combinations thereof.

6. The method of claim 2 wherein the step of forming the compactable granular mixture comprises dissolving the therapeutic compounds in a liquid and removing the liquid to form the granular mixture.

7. The method of claim 6 wherein the granular mixture is agglomerated prior to the compressing.

8. The method of claim 2 wherein the granular mixture is formed by the steps comprising mixing the therapeutic compounds to form a dry blend, wherein the therapeutic compounds contain a total of at least about 4 wt % moisture; compacting the dry blend under pressure to form the granular mixture; and reducing the particle size of the granular mixture prior to the compressing.

9. The method of claim 1 wherein the tablets formed have a friability of less than about 1 weight percent, and an increased hardness of at least about 10% relative to a tablet of the same weight, shape, and size, compressed under the same conditions, and not containing the compaction enhancing therapeutic compound.

10. The method of claim 9 wherein the compaction enhancing therapeutic compound is selected from the group consisting of glycosaminoglycans; herbal based extracts; botanical based extracts; vitamins; salt forms of minerals; anti-inflammatory agents; antibiotics; cholesterol lowering agents; and combinations thereof.

11. The method of claim 10 wherein the glycosaminoglycan is heparin, dermatan sulfate, chondroitin, sulodexide or a pharmaceutically acceptable salt thereof; the herbal or botanical based extract is St. John's Wort extract, horse chestnut, ginseng, ginko biloba, grape seed extract or a pharmaceutically acceptable salt thereof; the vitamin is niacinamide ascorbate or a pharmaceutically acceptable salt thereof; the anti-inflammatory agents is naproxen or a pharmaceutically acceptable salt thereof; the antibiotic is cephalosporin or a pharmaceutically acceptable salt thereof; the cholesterol lowering agent is cholestyramine or a pharmaceutically acceptable salt thereof.

12. The method of claim 11 wherein the compaction enhancing therapeutic compound comprises a glycosaminoglycan, grape seed extract, or combinations thereof.

13. The method of claim 9 wherein the other therapeutic compound is a non-compaction enhancing therapeutic compound.

14. The method of claim 13 wherein the compaction enhancing therapeutic compound comprises a glycosaminoglycan and the other therapeutic compound comprises an aminosugar.

15. The method of claim 14 wherein the glycosaminoglycan is heparin, dermatan sulfate, chondroitin, sulodexide, or a pharmaceutically acceptable salt thereof, and the aminosugar is glucosamine, or a pharmaceutically acceptable salt thereof.

16. The method of claim 15 wherein the glycosaminoglycan is chondroitin or a pharmaceutically acceptable salt thereof and the glucosamine is N-acetyl glucosamine sulfate, glucosamine hydrochloride, or glucosamine sulfate.

17. The method of claim 14 wherein the tablet formed comprises from about 3 weight percent to about 99.5 weight percent glycosaminoglycan; and from about 0.5 weight percent to about 97 weight percent aminosugar.

18. The method of claim 17 wherein the tablet formed further comprises at least a third therapeutic compound selected from the group consisting of kelp, manganese ascorbate, sodium ascorbate, calcium ascorbate, Vitamin C, dried powder forms of Vitamin A, Vitamin D, Vitamin E, Vitamin K, and beta carotene; Vitamin $B_6$, niacin, phosphorous containing salts, zinc containing salts, copper containing salts, calcium containing salts, calcium citrate, calcium carbonate, oyster shell, magnesium, manganese sulfate, boron, estrogen, and combinations thereof.

19. The method of claim 1 wherein the tablet composition formed comprises less than about 10 percent by weight of excipients, based on the total weight of the tablet.

20. The method of claim 19 wherein the tablet composition formed comprises less than about 5 percent by weight of excipients, based on the total weight of the tablet.

21. The method of claim 20 wherein the tablet formed comprises a lubricant.

22. A tablet produced by the process of claim 1.

23. A method of making a tablet comprising the steps of:
(a) forming a compactable granular mixture comprising (i) at least about 3 weight percent of a compaction enhancing therapeutic compound that is a glycosaminoglycan, (ii) at least one other therapeutic compound that is an amino sugar; and (iii) less than about 10 weight percent of non-aesthetic excipients; and
(b) compressing the granular mixture to form one or more tablets.

24. A tablet composition comprising:
(a) from about 3 weight percent to about 99.5 weight percent of a compaction enhancing therapeutic compound;
(b) from about 0.5 weight percent to about 97 weight percent of at least one second therapeutic compound that is different from the compaction enhancing therapeutic compound, wherein the compaction enhancing therapeutic compound enhances the compaction of the second therapeutic compound; and
(c) less than about 15 weight percent excipients.

25. The tablet composition of claim 24 wherein the compaction enhancing therapeutic compound is in intimate admixture with the second therapeutic compound.

26. The tablet composition of claim 24 wherein the tablet composition has a friability of less than about 1 weight percent, and an increased hardness of at least about 10% relative to a tablet of the same weight, shape, and size, compressed under the same conditions, and not containing the compaction enhancing therapeutic compound.

27. The tablet composition of claim 26 wherein the compaction enhancing therapeutic compound is selected from the group consisting of glycosaminoglycans; herbal based extracts; botanical based extracts; vitamins; salt forms of minerals; anti-inflammatory agents; antibiotics; cholesterol lowering agents; and combinations thereof.

28. The tablet composition of claim 27 wherein the glycosaminoglycan is heparin, dermatan sulfate, chondroitin, sulodexide or a pharmaceutically acceptable salt thereof; the herbal or botanical based extract is St. John's Wort extract, horse chestnut, ginseng, ginko biloba, grape seed extract or a pharmaceutically acceptable salt thereof; the vitamin is niacinamide ascorbate or a pharmaceutically acceptable salt thereof; the anti-inflammatory agents is naproxen or a pharmaceutically acceptable salt thereof; the antibiotic is cephalosporin or a pharmaceutically acceptable salt thereof; the cholesterol lowering agent is cholestyramine or a pharmaceutically acceptable salt thereof.

29. The tablet composition of claim 28 wherein the compaction enhancing therapeutic compound comprises a glycosaminoglycan, grape seed extract, or combinations thereof.

30. The tablet composition of claim 26 wherein the second therapeutic compound is a non-compaction enhancing therapeutic compound.

31. The tablet composition of claim 30 wherein the compaction enhancing therapeutic compound comprises a glycosaminoglycan and the second therapeutic compound comprises an aminosugar.

32. The tablet composition of claim 31 wherein the glycosaminoglycan is heparin, dermatan sulfate, chondroitin, sulodexide, or a pharmaceutically acceptable salt thereof, and the aminosugar is glucosamine, or a pharmaceutically acceptable salt thereof.

33. The tablet composition of claim 32 wherein the glycosaminoglycan is chondroitin or a pharmaceutically acceptable salt thereof and the glucosamine is N-acetyl glucosamine sulfate, glucosamine hydrochloride, or glucosamine sulfate.

34. The tablet composition of claim 31 wherein the tablet composition comprises from about 3 weight percent to about 99.5 weight percent glycosaminoglycan; and from about 0.5 weight percent to about 97 weight percent aminosugar.

35. The tablet composition of claim 31 wherein the tablet composition further comprises at least a third therapeutic compound selected from the group consisting of kelp, manganese ascorbate, sodium ascorbate, calcium ascorbate, Vitamin C, dried powder forms of Vitamin A, Vitamin D, Vitamin E, Vitamin K, and beta carotene; Vitamin $B_6$, niacin, phosphorous containing salts, zinc containing salts, copper containing salts, calcium containing salts, calcium citrate, calcium carbonate, oyster shell, magnesium, manganese sulfate, boron, estrogen, and combinations thereof.

36. The tablet composition of claim 31 wherein the amount of the excipient is less than about 5 weight percent.

37. The tablet composition of claim 36, wherein the excipient comprises a lubricant.

38. A tablet composition comprising:
(a) from about 5 weight percent to about 50 weight percent of a compaction enhancing therapeutic compound that is a glycosaminoglycan;
(b) from about 10 weight percent to about 95 weight percent of at least one second therapeutic compound that is an aminosugar, wherein the compaction enhancing therapeutic compound enhances the compaction of the second therapeutic compound and is in intimate admixture with the second therapeutic compound; and
(c) less than about 10 weight percent excipients.

* * * * *